United States Patent [19]

Glassey

[11] Patent Number: 5,447,063

[45] Date of Patent: Sep. 5, 1995

[54] LIQUID DENSITY MONITORING APPARATUS

[75] Inventor: Eugene A. Glassey, San Diego, Calif.

[73] Assignee: Fluid Data Systems, San Diego, Calif.

[21] Appl. No.: 852,565

[22] Filed: Mar. 17, 1992

[51] Int. Cl.$^6$ .............................................. G01N 9/10
[52] U.S. Cl. .......................................... 73/437; 73/433
[58] Field of Search ................... 73/437, 433, 434, 452, 73/453

[56] References Cited

U.S. PATENT DOCUMENTS

| | | | |
|---|---|---|---|
| 1,210,180 | 12/1916 | Logan | 73/452 X |
| 1,272,605 | 7/1918 | Becker | 73/437 |
| 1,800,532 | 4/1931 | Howard | 73/452 |
| 1,892,839 | 1/1933 | Howard | 73/452 X |
| 3,089,502 | 5/1963 | Davidson et al. | 137/91 |
| 3,186,423 | 6/1965 | Davidson et al. | 137/91 |
| 3,308,991 | 3/1967 | glassey | 222/57 |
| 3,323,368 | 6/1967 | Glassey | 73/401 |
| 3,377,869 | 4/1968 | Glassey | 73/453 |
| 3,407,666 | 10/1968 | Glassey | 73/452 |

OTHER PUBLICATIONS

"A Re-examination of the Plummet method for Determining Sediment Concentration", Joseph J. Szalona, *Instrument news*, Dc. 1989, pp. 4–5.

*Primary Examiner*—Hezron E. Williams
*Assistant Examiner*—Christine K. Oda
*Attorney, Agent, or Firm*—Brown, Martin, Haller & McClain

[57] ABSTRACT

A liquid bulk density monitoring apparatus which is particularly suitable for monitoring suspended sediment levels has a plummet suspended from one end of a balance beam and submerged in a vessel containing a liquid to be monitored. A sensor detects tilting of the beam from a reference or balance position as a result of variation in the sample bulk density, and produces an output to an output device for recording density variations. The apparatus is designed to compensate automatically for any changes in temperature, for example by making the plummet of a material having a coefficient of thermal expansion substantially the same as that of the liquid being monitored.

10 Claims, 2 Drawing Sheets

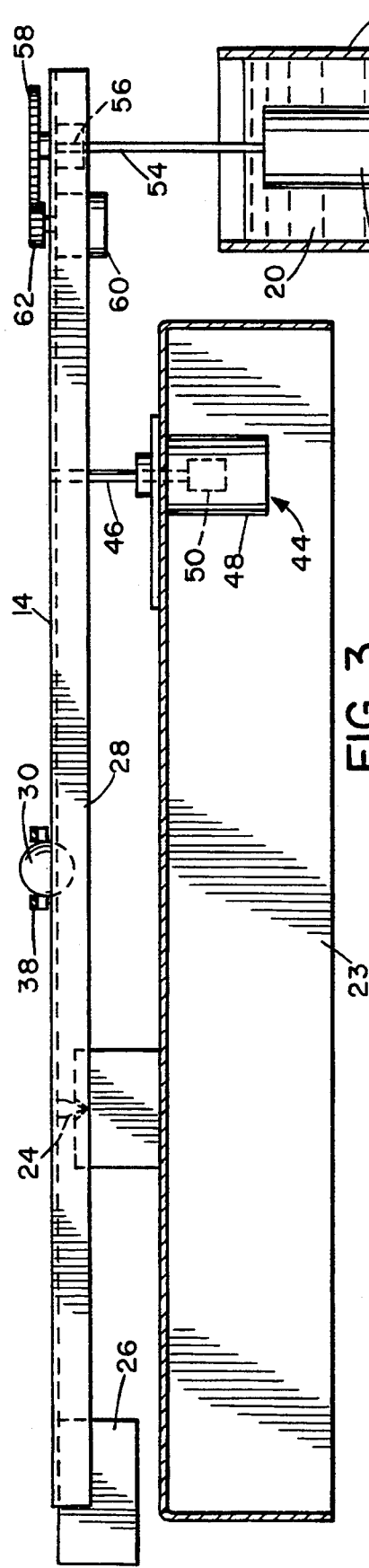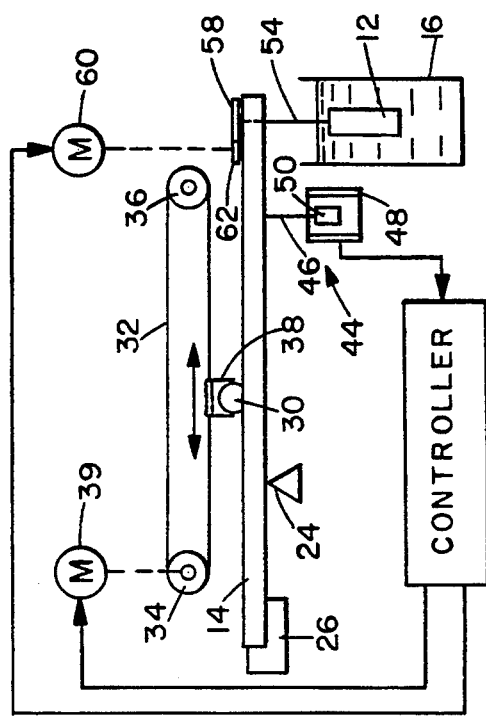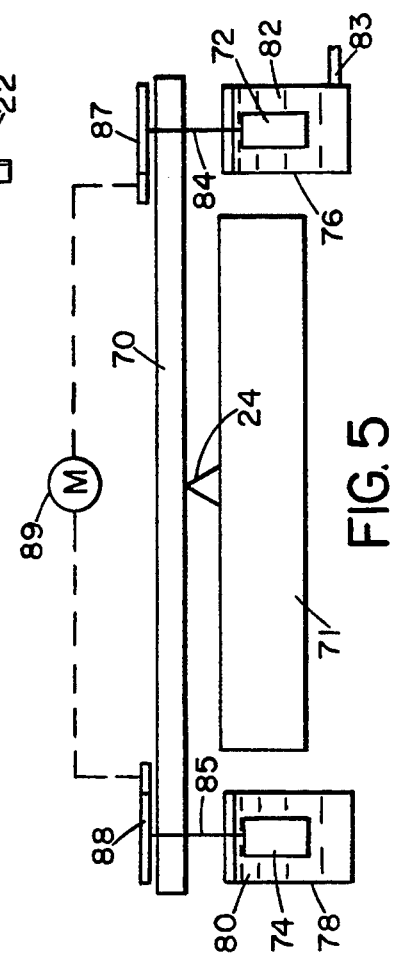

LIQUID DENSITY MONITORING APPARATUS

BACKGROUND OF THE INVENTION

The present invention relates generally to liquid density monitoring apparatus and is particularly concerned with monitoring suspended sediment concentration in water for hydrologic purposes.

Density monitors typically employ a hydrometer bulb floating or suspended in the liquid to be monitored. The elevation of the bulb in the liquid will be a direct function of the density. Various techniques have been used to monitor change in level of a hydrometer bulb in a liquid. For example, in U.S. Pat. No. 3,089,502 of Davidson et al., the bulb has an elongated stem with a magnetic core at its upper end which is vertically slidable relative to the core of a differential transformer, so that the change in current through the transformer will be proportional to the change in level of the hydrometer bulb. A similar arrangement utilizing a differential transformer to monitor bulb level is described in U.S. Pat. No. 3,407,666 of Glassey, where the hydrometer bulb is of stainless steel and/or Teflon ®. U.S. Pat. No. 3,186,423 of Davidson and Glassey describes another density control instrument employing a suspended hydrometer bulb having a magnetic core slidable within the coils of a differential transformer. In this instrument, temperature compensation is provided since the density of a liquid will be a function of its temperature. A coil link supporting the armature or magnetic core is of a material which expands and contracts in response to temperature change, thus changing the length of the coil and the core position as a function of temperature change. The armature is therefore raised or lowered to compensate for temperature variations, making the output essentially independent of temperature changes.

Another technique which has been proposed for measuring liquid density uses a plummet suspended from a mechanical balance into the liquid being monitored, with the effective weight of the plummet being a function of the density. Liquid density is related to the concentration of suspended sediment in a liquid, and it has therefore been proposed that such a technique be used to monitor sediment concentration in bodies of water such as rivers, for example. As a liquid becomes more dense due to increased sediment levels, the buoyant force acting on the plummet increases, decreasing its effective weight. Thus, the variation in the plummet weight from a reference value will be proportional to the bulk density, and thus the sediment concentration. However, one problem with using a standard mechanical balance to measure such effects is that the accuracy is very limited. Additionally, temperature variations will effect the accuracy of the output.

SUMMARY OF THE INVENTION

It is an object of the present invention to provide a new and improved liquid density monitoring apparatus.

According to the present invention, liquid density monitoring apparatus is provided which comprises a support frame, a beam supported on the frame for tilting movement about a fulcrum, a first weight suspended from the beam on one side of the fulcrum, and a bulb or plummet suspended from the beam on the other side of the fulcrum. A container for a liquid to be monitored is positioned below the beam for receiving the bulb so that the bulb is suspended in the liquid. A suitable measuring device is provided to measure tilting movement of the beam from a balance position in response to change in the effective weight of the bulb in the liquid, and to provide an output reading proportional to the change in bulb weight. Preferably, a poise is movably mounted for movement along the beam and a drive mechanism is associated with the poise for driving the poise along the beam. A sensor device is provided for sensing position of the beam relative to a null position, and is connected to control the drive mechanism to drive the poise to the null position. A readout device is driven by the motor to produce an output proportional to the movement of the poise.

An initial zero or reference position may be set up using pure water as the liquid, or any other desired reference. In the former case, the readout will be proportional to change in density from the pure water density, and hence will be proportional to the amount of suspended sediment in the water.

Preferably, the plummet or bulb is of a material which has a thermal coefficient of volumetric expansion which is a very close approximation to the value for water. One suitable material which has a thermal coefficient of expansion closely matching that of water is PVC or polyvinyl chloride. In this case, the plummet will expand and contract with temperature changes in equal proportion to the surrounding water, so that there is no net change of buoyancy and the output will be temperature compensated. In one preferred embodiment of the invention, the plummet comprises a hollow, cylindrical member of the selected material with plugs at each end. The walls of the plummet are preferably relatively thin, so that they will rapidly assume the same temperature as the surrounding water. Clearly, if a liquid other than water is being monitored, a different material will be selected for the bulb which has a coefficient of thermal expansion close to that of the liquid being monitored.

In one embodiment, the first weight suspended on one side of the beam is a fixed weight. In an alternative embodiment, identical plummets are suspended from the beam on both sides of the fulcrum, and vessels are located underneath the beam to locate the two plummets. One vessel contains a pure sample of the liquid. The other vessel contains a sample of liquid being monitored. The two plummets exert moments on the opposite ends of the beam balance in proportion to their effective weights. The change in buoyancy due to temperature change will be the same on each side, so that temperature effects are cancelled out.

This apparatus may be used in many different fields where the density of a liquid must be monitored for various reasons. For example, it may be used to monitor suspended sediment concentrations along rivers and in other hydrologic water sources such as lakes, underground water, oceans, and so on. The sample chamber would be connected to the water source in order to pump a sample into the chamber at periodic intervals. Once measured, the sample would be drained off. By collecting data along a river bed, for example, information on erosion and pollution sources can be extracted. The apparatus may also be useful for density monitoring in process control, tank gauging, and other areas.

BRIEF DESCRIPTION OF THE DRAWINGS

The present invention will be better understood from the following detailed description of some preferred embodiments of the invention, taken in conjunction with the accompanying drawings, in which like reference numerals refer to like parts, and in which:

FIG. 3 is a section on the lines 3—3 of FIG. 2;

FIG. 4 is a schematic block diagram of the detector system for detecting beam tilt and providing control signals to drive the servomotor and provide a data output; and FIG. 5 is a view similar to FIG. 3 illustrating a density monitoring apparatus with an alternative means of temperature compensation.

DESCRIPTION OF THE PREFERRED EMBODIMENTS

Figure 1:
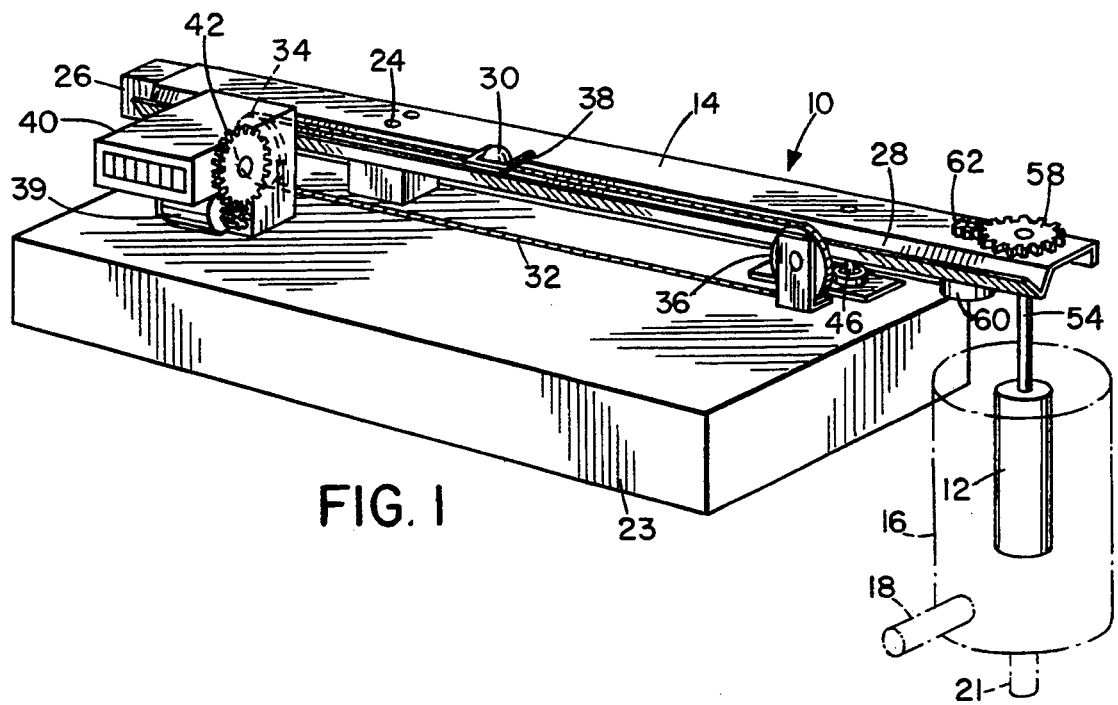
FIG. 1 is a perspective view of a liquid density monitoring apparatus according to a preferred embodiment of the present invention.

FIGS. 1–4 illustrate a density monitoring apparatus 10 according to a first embodiment of the present invention. The apparatus basically comprises a hydrometer bulb or plummet 12 suspended from one end of a balance beam 14 to extend into a specimen chamber or vessel 16 having an inlet 18 for receiving a liquid sample 20 to be tested. A drain outlet 21 is provided for draining tested samples from the chamber. The balance beam is supported on a base 23 for tilting movement about a fulcrum 24, and has a fixed weight 26 mounted at the opposite end of the beam to the hydrometer bulb 12. The end of the beam from which the bulb 12 is suspended projects out to one side of the base 23 over specimen vessel 16.

The balance beam is a modification of the balance beam manometer apparatus described in my U.S. Pat. Nos. 4,266,430 entitled "Precision Pressure-Responsive Fluid Gauge" and 4,277,981 entitled "Lead Screw Actuated Fluid Gauge". The beam has a V-groove 28 extending along its length along which a ball poise 30 rolls to establish balance of the beam. The ball poise 30, which may be a glass marble, is linked to an endless drive chain 32 extending around rotatably mounted drive and driven sprockets 34, 36 at opposite ends of the beam. The poise 30 is linked to the chain via U-shaped claw 38 which extends across V-groove 28 to loosely embrace the poise. Drive sprocket 34 is driven by servomotor 39, which is also connected to an output or data acquisition device 40, for example a mechanical counter or other data output device. In the illustrated embodiment, device 40 is a mechanical counter driven by servomotor 39 via gears 42.

A null sensor assembly 44 of the type described in my U.S. Pat. Nos. 4,266,430 and 4,277,981 is mounted at one end of the beam in order to detect displacement of the beam from a null or balanced position, as illustrated in FIGS. 3 and 4. The sensor assembly employs a differential transformer which is connected via suitable controller 49 to the servomotor 39 in order to drive the poise along the beam until the null position is reached, as schematically illustrated in FIG. 3. A threaded rod 46 is suspended from the beam and extends downwardly into transformer coil 48. A magnetic core or armature 50 is mounted on the lower end of rod 46. The secondaries of the transformer are connected so as to have a zero net output when armature 50 is electrically centered. As in U.S. Pat. Nos. 4,266,430 and 4,277,981, the net output of the transformers is connected via controller circuitry 49 to operate the servomotor. The system therefore operates to detect tilting of the beam and to drive the poise along the beam in a direction opposing the tilt until a null position is reached. The data output device then gives an output proportional to the distance travelled by the poise, which will be proportional to the tilting moment.

Figure 2:
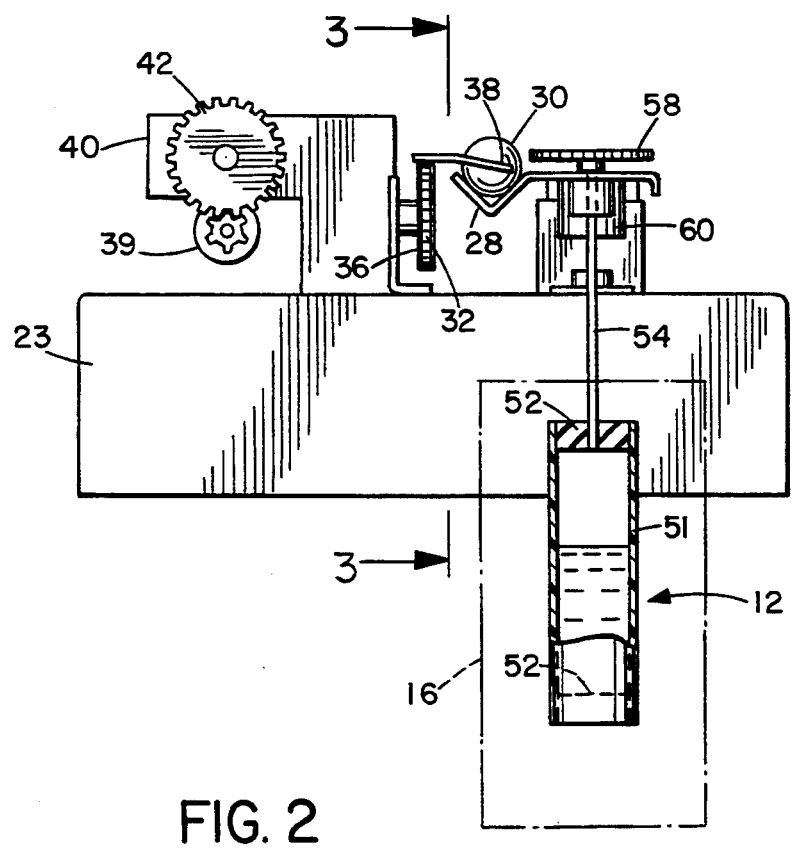
FIG. 2 is an end view of the apparatus.

The submerged bulb or plummet 12 is illustrated in more detail in FIGS. 2 and 3, and basically comprises a hollow, thin-walled tubular or cylindrical member 51 having plugs 52 at each end. The material of bulb 12 is selected to have a coefficient of thermal expansion which is a very close approximation to that of the liquid to be monitored. Where the monitored liquid is water, PVC or polyvinyl chloride material has been found to be a very good choice of material for the plummet, since it provides a close match to the thermal coefficient of volumetric expansion of water and is a suitably inert material for the plummet. Pure water has a coefficient of volumetric thermal expansion equal to 1.000115 cubical inches per °F., whereas PVC has a coefficient of volumetric thermal expansion approximating to 1.000117 cubical inches per °F. In alternative embodiments mixtures of materials may be used in order to provide an overall coefficient of thermal expansion which is even closer to that of water, or to that of other liquids to be monitored. Other suitable materials having a thermal coefficient of expansion close to that of water include acrylic and polycarbonate materials.

A rigid, coaxial stem 54 of the same material as bulb 12 extends upwardly from the bulb through an opening or through bore 56 at one end of the beam, and a gear wheel 58 is mounted at the upper end of stem 54. Gear wheel 58 is linked to a small motor 60 mounted in the end of the beam via drive gear 62, so that operation of motor 60 will act to spin the stem and attached hydrometer bulb 12. Motor 60 may be controlled by controller 49, as illustrated schematically in FIG. 4.

Operation of the apparatus will now be described in more detail. The apparatus is first calibrated so that the a zero or reference value for a pure sample of the liquid to be monitored can be established. This is done by supplying a fixed quantity of pure liquid to the sample chamber, and adding a counterweight to the beam to establish an initial system zero or reference value. When the apparatus has been calibrated so that the zero or null position is equivalent to the weight of the plummet in a pure sample of the liquid to be monitored, a specimen of the liquid to be sampled is pumped or otherwise placed in the sample chamber. Any variation in the liquid bulk density from that of a pure sample of the liquid will change the buoyancy force and thus the effective weight of the plummet, causing the balance to tilt from the null position by an amount proportional to the change in weight. The effective weight of the bulb or plummet 12 may be affected by any air bubbles or other particles adhering to the outside surface of the bulb, which could cause inaccuracy in the end result. Thus, prior to taking any reading, the motor 60 is actuated for a short time to spin the plummet in the liquid, causing any bubbles or other particles to be dislodged. This also acts to stir the liquid in the sample chamber, deterring settling of any suspended sediment which would produce an inaccurate output reading.

When the effective weight of the plummet changes, as noted above, the beam will tilt. The null sensor will simultaneously detect the tilting movement and operate motor 38 to drive the poise 30 in the opposite direction in order to offset the tilting moment and restore the beam to the null position. An output reading proportional to the distance moved by the poise from the previously established reference position will be provided at the data output device 40, and may also be provided to suitable data storage device such as an electronic data logger or recorder or the like. After the reading has been taken, the sample is drained from the chamber by any suitable means, and a new sample is supplied to the chamber after a predetermined interval. This allows the sediment level in a body of water or other liquid to be monitored and the output information collected at predetermined intervals. The liquid sampling and draining, as well as operation of motor 60 to spin the plummet for a short interval after each sample is supplied to the chamber, may be done automatically by a suitable automatic control system.

Since the plummet is of a material having a coefficient of thermal expansion very close to that of water, any changes in water density resulting from temperature changes will produce negligible change in the output. This is because the plummet will expand and contract with temperature change in equal proportion to the expansion and contraction of the surrounding water, so that there is no net change in buoyancy and thus no change in the effective weight of the plummet. The plummet walls are made thin so that they will assume the temperature of the surrounding water relatively quickly.

This apparatus therefore allows the bulk density of a liquid to be monitored to produce an output which is more or less independent of temperature changes. Errors arising from air bubbles or foreign matter clinging to the plummet and changing its effective weight are also significantly reduced or eliminated using this apparatus, producing more accurate results.

In one specific example of the apparatus described above the sample chamber was relatively small, and was sized to contain a 12 oz sample of liquid. With a poise weight of 6.070 grams, and a plummet of diameter 1.050 inches, height 4.275 inches, and volume 3.702 cubic inches, an output having an accuracy of the order of 10 milligrams per liter of suspended sediment concentration was achieved.

FIG. 5 illustrates an alternative embodiment of the invention in which a different method of temperature compensation is used. This alternative may be used for liquids other than water. In this arrangement, a balance beam apparatus similar to that illustrated in FIG. 1 is used, and like reference numerals have been used for like parts as appropriate. However, balance beam 70 projects outwardly from both ends of the base 71, and a plummet 72, 74 is suspended from each end of the beam into a container or vessel 76, 78, respectively, for holding a liquid sample. The two plummets 72 and 74 are manufactured to be as nearly identical as practical. A pure sample 80 of the liquid to be monitored is supplied to one of the vessels 76, while a sample 82 to be measured for density or suspended sediment content is supplied to the vessel 78 via inlet 83. Since both vessels contain the same liquid, the buoyancy level will change equally in each vessel with temperature changes. The two plummets will exert moments on the two ends of the beam 70 in the same manner as two weights on the weigh pans of a beam balance used for weighing. Thus, the plummet in the pure sample 80 will introduce temperature compensation by offsetting any change in buoyancy of the sample being measured as a result of temperature changes. As in the previous embodiment, each plummet has a stem 84, 85 projecting up through the beam and having a gear wheel 87, 88 at its upper end connected to a spin drive motor 89 for spinning both plummets for a short time before any reading is taken.

The apparatus in FIG. 5 otherwise operates in an identical manner to that of FIGS. 1–4, to detect tilting of the beam and produce an output signal to a data collecting device, and will therefore not be described in detail.

Although some preferred embodiments of the present invention have been described above by way of example only, it will be understood by those skilled in the field that modifications may be made to the disclosed embodiments without departing from the scope of the invention, which is defined by the appended claims.

I claim:

1. A liquid density monitoring apparatus for monitoring any change in density of a liquid as a result of change in sediment concentration in the liquid, comprising:

a support base;
a fulcrum mounted on the base;
an elongate balance beam pivotally supported on the fulcrum at an intermediate point in the length of the balance beam for tilting movement of the balance beam about the fulcrum;
a plummet suspended from the beam on one side of the fulcrum;
a sample vessel for containing a liquid sample positioned below the beam in alignment with the plummet to receive the plummet for submersion in said liquid sample in the vessel, said liquid sample having a density proportional to the sediment concentration in the liquid sample, whereby the plummet has an effective weight which varies as a function of the density of said liquid sample and temperature of said liquid sample;
a weight secured to the beam on the opposite side of the fulcrum to the plummet to counterbalance the plummet when the effective weight of the plummet is at a reference weight corresponding to a predetermined reference density of said liquid sample;
sensor means for sensing a null position of the beam and producing an output control signal proportional to tilting of the beam from the null position as a result of change in the effective weight of the plummet from said reference weight;
a poise movable along the beam to counterbalance tilting of the beam from the null position;
drive means linked to said sensor means and said poise for driving said poise along the beam in response to said output control signal until the null position is detected;
data output means linked to said drive means for producing an output proportional to said tilting movement of the beam as a result of change in the effective weight of the plummet; and
temperature responsive means for offsetting variations in the effective weight of the plummet as a result of temperature variations.

2. The apparatus as claimed in claim 1, wherein said plummet is made of a material having a thermal coefficient of volumetric expansion substantially equal to that of the liquid being monitored, said material comprising said temperature responsive means for producing expansion and contraction of the plummet in substantially equal proportion to the expansion and contraction of the volume of the liquid sample.

3. The apparatus as claimed in claim 2, wherein said plummet has a stem projecting upwardly towards said balance beam, said stem having an upper end and being secured to the beam at said upper end, the stem being of the same material as the plummet.

4. The apparatus as claimed in claim 1, wherein said plummet comprises a hollow cylindrical member having opposite ends and having end plugs sealing each of said opposite ends of said cylindrical member.

5. The apparatus as claimed in claim 1, including spin means for spinning said plummet prior to producing said output from said data output means.

6. The apparatus as claimed in claim 5, wherein said beam has an opening, and a plummet stem projects transversely through said opening, the plummet stem having an upper end above said beam and a lower end below said beam, the plummet being secured to the lower end of said stem, and the upper end of the stem being secured to said spin means.

7. The apparatus as claimed in claim 1, wherein said beam has a V-groove extending along the length of the beam, and said poise comprises a ball mounted for rolling movement along said V-groove, said drive means being linked to said ball.

8. The apparatus as claimed in claim 7, wherein said drive means comprises a pair of spaced drive and driven sprockets, a drive chain extending around said sprockets, and a motor for driving said drive sprocket, and a link member projecting from said chain across said V-groove for engaging said ball.

9. The apparatus as claimed in claim 8, wherein said link member has a pair of spaced fingers projecting transversely across said V-groove and embracing said ball.

10. The apparatus as claimed in claim 1, wherein said weight comprises an additional plummet suspended from the opposite side of the fulcrum to the first-mentioned plummet, and an additional sample vessel located beneath the beam for receiving the additional plummet and containing a reference pure sample of the liquid to be monitored, said additional plummet and said additional vessel comprising said temperature responsive means.

* * * * *